(12) United States Patent
Hughes et al.

(10) Patent No.: US 9,145,534 B2
(45) Date of Patent: Sep. 29, 2015

(54) FAT CONTAINING COMPOSITION

(75) Inventors: Adrian Hughes, The Hague (NL); Rakesh Kapoor, Saskatchewan (CA); Jeanette M Fusick, Saskatchewan (CA)

(73) Assignee: Bioriginal Food & Science Corporation, Saskatoon, Saskatchewan (CA)

( * ) Notice: Subject to any disclaimer, the term of this patent is extended or adjusted under 35 U.S.C. 154(b) by 989 days.

(21) Appl. No.: 12/309,787

(22) PCT Filed: Jul. 27, 2007
(Under 37 CFR 1.47)

(86) PCT No.: PCT/EP2007/006706
§ 371 (c)(1),
(2), (4) Date: Mar. 16, 2010

(87) PCT Pub. No.: WO2008/012106
PCT Pub. Date: Jan. 31, 2008

(65) Prior Publication Data
US 2010/0298274 A1   Nov. 25, 2010

(30) Foreign Application Priority Data

Jul. 28, 2006 (EP) ..................................... 06253965

(51) Int. Cl.
*A61K 31/66* (2006.01)
*A61K 31/20* (2006.01)
*C11B 5/00* (2006.01)
*A23L 1/30* (2006.01)

(52) U.S. Cl.
CPC ............. *C11B 5/0085* (2013.01); *A23L 1/3002* (2013.01); *A23L 1/3008* (2013.01); *C11B 5/0007* (2013.01); *C11B 5/0071* (2013.01)

(58) Field of Classification Search
None
See application file for complete search history.

(56) References Cited

U.S. PATENT DOCUMENTS

| 5,705,618 | A | | 1/1998 | Westcott et al. |
| 5,846,944 | A | | 12/1998 | Prasad |
| 5,895,652 | A | * | 4/1999 | Giampapa ................ 424/195.17 |
| 6,107,334 | A | | 8/2000 | Chilton |
| 7,048,960 | B2 | | 5/2006 | Pizzey |
| 2004/0048804 | A1 | | 3/2004 | Ahotupa et al. |
| 2004/0191396 | A1 | | 9/2004 | Barker |
| 2004/0208939 | A1 | | 10/2004 | Sears et al. |
| 2005/0129830 | A1 | * | 6/2005 | Koike et al. ................... 426/601 |
| 2005/0249860 | A1 | | 11/2005 | Konecsni et al. |

FOREIGN PATENT DOCUMENTS

| CA | 2 563 381 | * | 4/1997 | ............. A61K 36/55 |
| DE | 10204637 | | 11/2002 | |
| EP | 0906761 | | 4/1999 | |
| FR | 2851919 | | 9/2004 | |
| JP | 05 124958 | * | 5/1993 | ............. A61K 31/07 |
| WO | WO02/080702 | | 10/2002 | |
| WO | WO03/084974 | | 10/2003 | |
| WO | WO 2004/018598 | * | 3/2004 | ................ C11C 3/00 |
| WO | WO2004/094443 | | 11/2004 | |
| WO | WO2006/107820 | | 10/2006 | |

OTHER PUBLICATIONS

Bravi et al (Food Chem 126:1553-1558, 2011).*
www.vitamins-nutrition.org (accessed online, Dec. 14, 2012).*
www.digitalnaturopath.com (accessed Dec. 14, 2012).*
Patel et al (Int J Pharmceut Sci and Drug Res 4(1):15-18, 2012).*
Derwent Accession No. 1993-200436.*
European Search Report on EPO6 25 3965 dated Jan. 16, 2007.
Written Opinion of the international Searching Authority on PCT/EP2007/006706 dated Jan. 28, 2009.
International Search Report on PCT/EP2007/006706 dated Oct. 26, 2007.

* cited by examiner

*Primary Examiner* — Craig Ricci
(74) *Attorney, Agent, or Firm* — Ryan Kromholz & Manion, S.C.

(57) ABSTRACT

A composition comprises a fat phase wherein the fat phase comprises: more than 10 wt. % DHA and/or EPA or derivatives thereof; or more than 5 wt. % GLA or a derivative thereof; or more than 10 wt. % of GLA, EPA and/or DHA in total or derivatives thereof; and secoisolariciresinol (SECO) or a derivative thereof, with the proviso that when the composition comprises GLA, the composition is substantially free of isoflavones. The composition and mixtures or blends comprising the composition may be used for the treatment of PMS and prostate conditions.

5 Claims, 12 Drawing Sheets

FAT CONTAINING COMPOSITION

This invention relates to a composition, mixture, blend, foodstuff and food supplement comprising certain essential fatty acids and phytochemicals and the use of these for the treatment of certain conditions.

The long chain fatty acids eicosapentaenoic acid (EPA) and docosahexaenoic acid (DHA) are important in maintaining the integrity and fluidity of the membrane which surrounds human cells. In particular, DHA is crucial to the optimal development of the brain and eyes.

These acids cannot be synthesised by the human body and so need to be included in the diet. EPA and DHA are generally considered to have health benefits and are available in the form of supplements. Gamma linolenic acid (GLA) is also believed to provide certain health benefits.

DHA and EPA can be obtained from, for example, fish oils. When obtaining food oils and fats from animal, vegetable and marine sources, it is desirable to produce edible oil and fat products that have a bland neutral taste for at least several months after processing. It is usually essential to remove compounds that give flavour to the oil as well as compounds that are detrimental to stability.

Oils containing EPA, DHA and GLA can be unstable and susceptible to deterioration because of the highly unsaturated nature of these fatty acids. The oils of marine origin also have a very intense fishy odour and taste. The odour and taste compounds and their precursors must usually be removed to extremely low levels to make the oil more suitable for food and nutritional uses and to improve their flavour stability.

Thus, the stability of oils and compositions, such as, for example, food supplements, comprising long chain unsaturated ω-3 and ω-6 acids such as EPA, DHA and GLA remains a problem.

WO 2004/094443 A1 discloses a method for recovering a secondary plant metabolite of a phenolic nature from a seed material and an extract comprising the secondary plant metabolite. Specific foodstuffs, cosmetics and medicaments are also disclosed.

WO 02/080702 A1 describes the use of specific lignans in food products to provide certain health benefits, such as anti-aging and anti-inflammatory properties. According to this document, the lignans can also provide effects upon a number of physical parameters or characteristics of food products.

DE 102 04 637 A1 discloses a pharmaceutical, nutritional or food additive composition containing gamma-linolenic acid, isoflavone and lignan, that is stated to be effective e.g. against tumors, osteoporosis and premenstrual syndrome.

According to a first aspect of the invention, there is provided a composition comprising a fat phase wherein the fat phase comprises: more than 10 wt. % DHA and/or EPA or derivatives thereof; or more than 5 wt. % GLA or a derivative thereof; or more than 10 wt. % of GLA, EPA and/or DHA in total or derivatives thereof; and secoisolariciresinol (SECO) or a derivative thereof, preferably with the proviso that when the composition comprises GLA, the composition is substantially free of isoflavones. For the composition, the wt. % is based on the total weight of the fat phase.

In a further aspect of the invention, there is provided a mixture comprising a composition according to the invention and an additive selected from the group consisting of phospholipids, antioxidants and partial glycerides and combinations thereof.

In another aspect of the invention, there is provided a blend comprising:
(i) 0.3 to 95 wt. % (based on the total weight of the blend) of the composition according to the invention or the mixture according to the invention, and
(ii) 5 to 99.7 wt. % (based on the total weight of the blend) of a complementary fat, having an N value (solid fat content NMR-pulse; not stabilized) of more than 15 at 20° C., preferably more than 20.

N-values refer to solid fat contents measured by NMR pulse techniques on unstabilized fats. Unstabilized means that the fat is melted at 80° C., kept at 60° C. for 5 minutes, cooled to 0° C. and kept at 0° C. for 1 hour and kept at measurement temperature for 30 minutes.

The $N_{20}$ value of the complementary fat is preferably from 15 to 90, more preferably from 40 to 80, in particular from 45 to 75.

In another aspect of the invention, there is provided a foodstuff or food supplement comprising the composition, mixture or the blend according to the invention.

In yet another aspect of the invention, there is provided a method of preventing or treating PMS, in a human, or of treating or ameliorating the symptoms of PMS in a human, which comprises administering to said human an effective amount of: the composition, the mixture, the blend or the foodstuff or food supplement, or mixtures thereof according to the invention.

In a still further aspect of the invention, there is provided a method of preventing or treating a prostate condition, in a human patient, or of treating or ameliorating the symptoms of a prostate condition in a human patient, which comprises administering to said patient an effective amount of: the composition, the mixture, the blend or the foodstuff or food supplement, or mixtures thereof according to the invention.

In another aspect of the invention, there is provided the use of secoisolariciresinol (SECO) or a derivative thereof to improve the stability and/or sensory properties and/or nutritional activity of: a ω-3 and/or a ω-6 fatty acid, or a derivative thereof: or a composition comprising said fatty acids in a fat phase.

Figure 1:
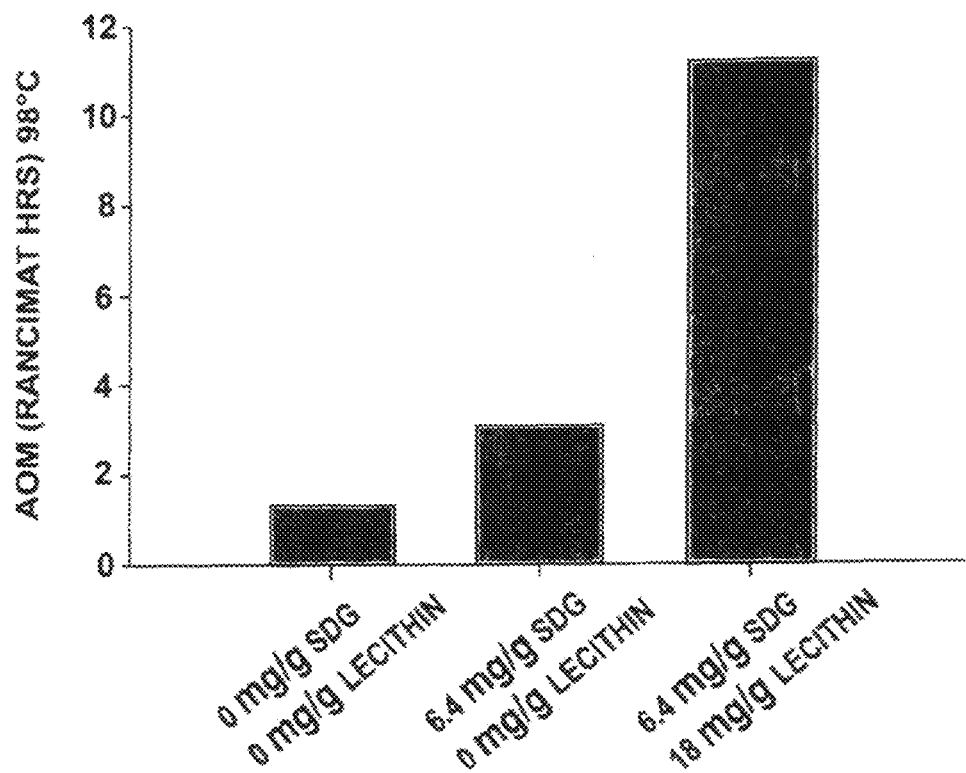
FIG. 1 shows the resistance to oxidation with addition of lecithin to a blend of fish oil 1812TG with 6.4 mg SDG/g oil, in the form of a graph.
Figure 2:
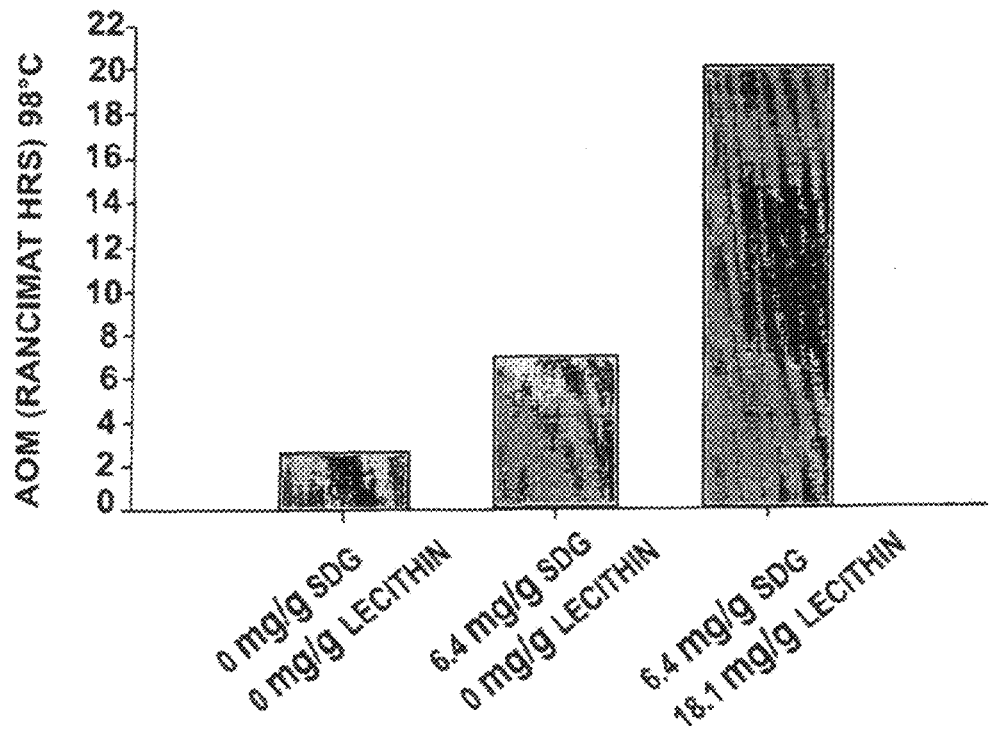
FIG. 2 shows the resistance to oxidation with addition of lecithin to a blend of fish oil and borage oil (50:50 ratio) containing 6.4 mg SDG/g oil, also in the form of a graph.
Figure 3:
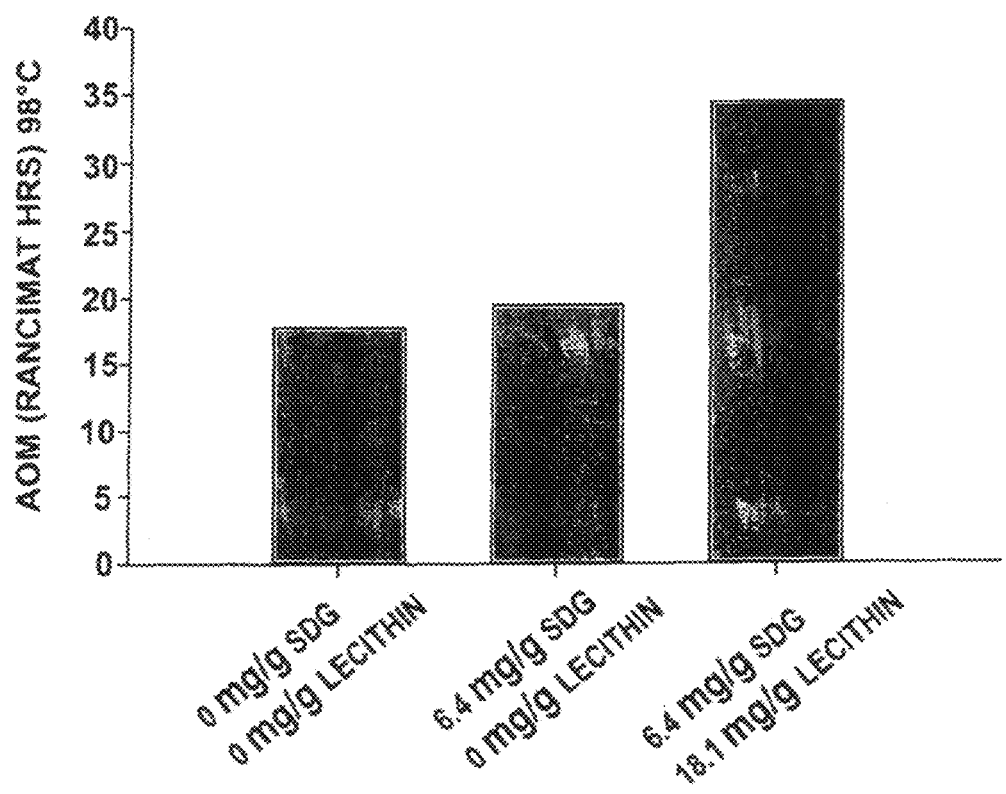
FIG. 3 shows the resistance to oxidation with addition of lecithin to a blend of borage oil containing 6.4 mg SDG/g oil, in the form of a graph.

The composition of the invention may comprise or consist of a continuous fat phase. Preferably the composition is a single phase. Alternatively, the composition may also comprise a separate non-fat phase i.e., a continuous or discrete phase which comprises substantially no fat components. By "substantially", it is intended to mean that the fat content of the non-fat phase comprises less than 10 wt. % fat, preferably less than 5 wt. % fat, more preferably, less than 1 wt. % fat. In one embodiment, the fat content of the non-fat phase is less than 0.1 wt. % fat, such as about 0%. The non-fat phase may be in a solid form or a liquid form. In one embodiment of the invention, the composition comprises a non-fat liquid phase, which is preferably separate. The liquid phase may be aqueous. The aqueous phase may comprise water in an amount of from 0.1 to 99 wt. %, preferably 5 to 90 wt. %, more preferably from 10 to 50 wt. %.

In one embodiment of the invention, the composition comprises a fat continuous emulsion. The composition of the invention may be in the form of a liquid or solid at room temperature i.e., from 0° C. to 30° C., preferably 10 to 20° C. Preferably, the composition is in the form of a liquid.

DHA and EPA for use in the invention can be found in, for example, natural fish oils, modified fish oil, fish oil concentrate, fractionated fish oil, enzymically treated fish oil or oils from microbial sources. The fish oil may contain other components in addition to EPA and DHA, such as antioxidants, for example, tocopherols.

Fish oil containing both EPA and DHA can be extracted from natural sources such as plankton and krill. EPA and DHA can also be fermented (e.g., from algae) under controlled conditions. In one embodiment, the extracted oil is refined to meet international standards for edible oils. The triglyceride form of fish oil can be modified either by chemical or biochemical means to produce free fatty acids, salts of free fatty acids, methyl or ethyl esters, or monoglycerides which can be further fractionated to give higher contents of EPA and DHA than the starting oil in the triglyceride form. Suitable EPA and DHA can also be chemically synthesized.

Suitable sources of GLA include, for example, borage oil, evening primrose oil, and blackcurrant oil. The borage oil may comprise other components in addition to GLA such as, for examples, other fatty acids, preferably palmitic acid, oleic acid, linoleic acid and erucic acid.

A number of seed sources such as borage, evening primrose, and blackcurrant are sources of GLA. GLA can also be made by fermentation with selected algae or bacterial strains. GLA in the triglyceride form can be extracted and refined from vegetable seed sources using standard technology to create edible oil. In one embodiment of the invention, GLA is obtained from borage, blackcurrant, evening primrose seeds or oat bran. Certain microorganisms can also be fermented to produce GLA in the triglyceride form and this can be refined to produce edible oil.

GLA isolated in the triglyceride form can be chemically or biochemically transformed into free fatty acids, salts of free fatty acids, methyl or ethyl esters, or monoglycerides which can be further fractionated by standard techniques into fractions with higher GLA content than found in the starting oils. Finally, GLA can be chemically synthesized by standard chemical techniques.

Natural oils, such as those indicated above, that are a source of DHA, EPA and GLA can be used directly in the compositions, mixtures and blends of the invention. However, concentration or isolation and/or modification of DHA, EPA and GLA in the natural oils prior to their use is also one embodiment of the invention.

Lignans are compounds that are present in a number of natural products such as flaxseed, tea and coffee. EP-A-906 761 describes the extraction of phytochemicals from plant matter, such as flax, and the teachings of this document are hereby incorporated by reference in their entirety. SECO is an example of a lignan. It is preferred that the SECO and the derivatives of SECO for use in the invention are obtainable, preferably obtained, from flax.

SECO or derivatives thereof, may be extracted from flax seed by contacting an oil free flax seed meal with an aliphatic alcohol as described in U.S. Pat. No. 5,705,618. Alternatively, lignans, such as SECO or derivatives thereof, may be extracted from seed material or a specific part of a suitable seed hull, as disclosed in WO 2004/094443. Suitable seed material for obtaining the SECO or derivative thereof for use in the invention includes seed materials derived from Linaceae, for example *Linum usitatissimum* L. (linseed and flax seed).

The SECO or a derivative thereof can be included in the composition in any suitable delivery form, for example, as a free compound, as a concentrate or an extract of a natural product, in particular as a concentrate of flaxseed, in encapsulated form, such as encapsulated in a sugar, starch or gelatine. The SECO or derivative thereof may also be added in the form of a powder or crystals, optionally on an edible carrier. The particle size of the SECO or a derivative thereof is preferably at least 50% through 80 mesh (US), more preferably at least 80%, most preferably at least 90%. Preferably, the SECO or derivative thereof is in the form of a powder.

By the term "stability" it is intended to mean one or more of: the physical stability (for example, the tendency of the EPA, DHA or GLA to produce free radicals and other by-products); sensory stability, such as maintaining an acceptable taste and/or other oral properties, such as smell, for humans, (i.e., the production of unacceptable flavours and odours from the EPA, DHA or GLA); and the stability of the nutritional activity of the EPA, DHA or GLA.

The invention can be considered to relate to the finding that SECO or a derivative thereof, preferably in combination with a phospholipid emulsifier, can stabilise oils, such as fish oil and borage oil and mixtures thereof, comprising DHA, EPA and/or GLA or derivatives thereof.

Derivatives of DHA, EPA, GLA and SECO include salts and esters thereof, or a mixture of two or more of these materials. Salts are non-toxic, pharmaceutically acceptable and/or acceptable for use in food products and/or pharmaceuticals and include, for example, salts with alkali metals and alkaline earth metals such as sodium, calcium and magnesium, preferably sodium. Esters include, for example, mono-, di- and tri-glycerides and mixtures thereof, and $C_1$ to $C_{20}$ alkyl esters, preferably $C_2$ to $C_6$ alkyl esters (where the alkyl group can be straight chain or branched), as well as esters formed with alcohols that are acceptable in food products or pharmaceutical products.

In one embodiment of the invention EPA, DHA, and GLA are in the form of triglyceride esters. Other preferred forms are methyl or ethyl esters, monoglycerides, free fatty acids, or the appropriate salts of free fatty acids, such as sodium salts.

Any mixture or combination of one or more, such as two, three or four, of the known geometrical isomers (such as, for example: cis, trans; cis, cis; or trans, trans) of EPA, DHA and GLA may be used in the compositions of the invention.

Other preferred derivatives of DHA, EPA and GLA include $C_{10}$-$C_{20}$ alkyl esters, mono-, di-, or triglycerides, or mixtures thereof.

In one embodiment of the invention, when the composition comprises GLA, the composition is preferably substantially free of isoflavones. By "substantially free", it is intended to mean that the amount of isoflavones is less than 10 wt. % based on the total weight of the composition, preferably less than 5 wt. %, more preferably less than 2 wt. %. It is even more preferred that the amount of isoflavones is less than 1 wt. %, such as less than 0.1 wt. % or 0.01 wt. %. In one embodiment of the invention, the composition is free of isoflavones i.e., the amount of isoflavones is about 0 wt. % when GLA is present.

The composition of the invention preferably does not comprise an isoflavone. The composition and, in particular, the fat phase of the composition preferably comprise as the sole phytoestrogen component SECO or a derivative thereof i.e., the phytoestrogen in the composition consists of SECO or a derivative thereof. The pharmaceutically active components in the composition preferably consist of DHA and/or EPA and/or GLA and SECO or a derivative thereof.

In one embodiment of the invention, the derivative of SECO is secoisolariciresinol diglucoside (SDG). A preferred source of SDG is that obtained as Linumlife™ Extra (Standardized Flax Lignan), comprising 20 wt. % lignans as SDG. Other derivatives of SECO may also be used.

In one embodiment, the composition comprises one or more of: borage oil, evening primrose oil, and blackcurrant oil; natural fish oils, modified fish oil, fish oil concentrate, fractionated fish oil, enzymically treated fish oil or oils from microbial sources, as a source of DHA and/or EPA and/or GLA, preferably in an amount of from 25 to 95 wt. %, more preferably from 40 to 75 wt. % by weight of the fat phase. In another embodiment of the invention, the composition comprises a mixture of borage oil (as a source of GLA) and fish oil (as a source of EPA and DHA), preferably in a weight ratio of from 1 to 5 to 5 to 1, more preferably from 1 to 2 to 2 to 1. In a particularly preferred embodiment, the weight ratio of borage oil to fish oil is about 1:1.

The fat phase preferably comprises at least 80 wt. % based on the total weight of the fat phase of triglycerides, preferably at least 90 wt. % triglycerides, most preferably at least 95 wt. % triglycerides as the derivatives of DHA, EPA and/or GLA. The amounts of DHA, EPA and/or GLA in the triglyceride form in the fat phase may be from 80 to 100 wt. %, more preferably from 85 to 95 wt. % based on the total weight of the fat phase.

It is preferred that the amount of SECO or a derivative thereof is sufficient to provide stabilisation of DHA, EPA and/or GLA, as defined above, as well as health benefits.

A single serving (or daily dose, preferably taken in one sitting) of each of borage oil (as a source of GLA) and fish oil (as a source of EPA and DHA) may be from 0.1 to 30 mg/kg body weight, preferably from 1 to 20 mg/kg, most preferably from 5 to 10 mg/kg body weight.

In one embodiment of the invention, the composition comprises at least 0.005 wt. %, based on the total weight of the fat phase, of SECO or a derivative thereof, such as SDG, preferably at least 0.3 wt. %, most preferably between 0.4 and 15 wt. %.

Advantageously, the fat phase of the composition comprises more than 20 wt. % based on the total weight of the fat phase, preferably more than 35 wt. %, most preferably between 40 and 80 wt. % of DHA and EPA or a derivative thereof.

The weight ratio of DHA to EPA may be that obtainable from fish oils. In an embodiment of the invention, the weight ratio of DHA to EPA in the fat phase is at least 2:1, preferably at least 3:1, most preferably between 4:1 and 12:1. Preferably the weight ratio is between 0.5:1 and 1:1.

In an alternative embodiment, the weight ratio of EPA to DHA in the fat phase is at least 2:1, preferably at least 3:1, most preferably between 4:1 and 12:1. Preferably the weight ratio is between 1:1 and 2.0:1.

The fat phase of the composition preferably comprises more than 8 wt. % of GLA based on the total weight of the fat phase, more preferably more than 15 wt. %, and most preferably between 20 and 50 wt. %.

The fat phase of the composition preferably comprises more than 15 wt. % based on the total weight of the fat phase, more preferably more than 35 wt. %, and most preferably between 40 and 80 wt. % of DHA, EPA and GLA in total.

The relative amounts of EPA, DHA and GLA may be any combination that produces the total level, e.g., DHA (5 wt. %), EPA (2 wt. %), GLA (4 wt. %) or DHA (10 wt. %), EPA (15 wt. %), GLA (10 wt. %).

The mixture of the invention comprises an additive selected from the group consisting of phospholipids, antioxidants and partial glycerides. The additive is preferably present in the composition in an amount of from 0.01 to 50 wt. %, by weight of the total composition, more preferably from 0.1 to 30 wt. % of the composition, most preferably from 1 to 10 wt. % of the composition.

It is preferred that the phospholipids, antioxidants and partial glycerides are edible i.e., non-toxic to humans. By "partial glycerides" it is intended to mean mono- or di-glycerides i.e., glycerides in which not all of the hydroxyl groups have been esterified i.e., one or any two of the hydroxyl groups.

In one aspect of the invention, there is provided a composition comprising a fat phase wherein the fat phase comprises: more than 10 wt. % DHA and/or EPA or derivatives thereof; or more than 5 wt. % GLA or a derivative thereof; or more than 10 wt. % of GLA, EPA and/or DHA in total or derivatives thereof; secoisolariciresinol (SECO) or a derivative thereof; and a phospholipid emulsifier.

The wt. % for DHA, EPA, GLA and SECO is based on the total weight of the fat phase. The phospholipid emulsifier is preferably present in the composition in an amount of from 0.01 to 50 wt. %, by weight of the total composition, more preferably from 0.1 to 30 wt. % of the composition, most preferably from 1 to 10 wt. % of the composition. This aspect of the invention includes all of the preferred combinations set out above for the composition, for example preferred wt. %, weight ratios, sources of materials and the nature of derivatives and additional components.

Suitable examples of phospholipids and phospholipid emulsifiers are those selected from the group consisting of lecithin, enzymically treated lecithin, fractions of lecithin or mixtures thereof. These compounds can be obtained commercially. The lecithin may, for example, be obtained from soy (soy lecithin) or sunflower (sunflower lecithin). Preferably the lecithin is obtained from soy. It may be unbleached. In one embodiment of the invention, a phospholipid, such as those indicated above, is used in combination with SECO or a derivative thereof to synergistically enhance the stability of EPA, DHA and/or GLA.

In one embodiment of the invention, the mixture comprises, preferably in addition to any of the above compositions, lecithin, enzymically treated lecithin, fractions of lecithin or mixtures thereof, preferably in an amount of from 0.001 to 10 wt. %, more preferably from 0.01 to 5 wt. %.

The weight ratio of SECO or a derivative thereof, such as SDG, to lecithin, such as soy lecithin, is preferably from 1:10 to 10:1, more preferably from 1:1 to 5:1, such as from 1.5:1 to 3:1.

When the composition comprises GLA, it is a preferred embodiment of the invention that lecithin is included within the composition, mixture or blend, as distinct from or in addition to a capsule i.e., such as a capsule coating or shell.

Preferred examples of partial glycerides are those selected from the group consisting of saturated and unsaturated monoglycerides, saturated or unsaturated diglycerides, or mixtures thereof with emulsifying properties. Suitable saturated and unsaturated parts can be those derived from $C_{10}$ to $C_{20}$, preferably $C_{12}$ to $C_{18}$ saturated or unsaturated fatty acids.

Examples of suitable antioxidants are those selected from the group consisting of natural or synthetic tocopherols, BHA, BHT, TBHQ, rosemary extracts or polyphenols, vitamin E and mixtures thereof. These compounds can be obtained commercially. A particularly preferred antioxidant comprises a mixture of one or more, preferably all, of rice bran oil, rosemary extract, mixed tocopherols, ascorbyl palmitate and citric acid.

In one embodiment of the invention, the mixture preferably comprises, in addition to the composition of the invention, an additive selected from lecithin, such as soy lecithin, and an antioxidant comprising rosemary extract and mixed tocopherols, such as Dadex RM.

A blend as defined above comprises a complementary fat. By "complementary fat", it is intended to mean a fat that is compatible with the composition or mixture of the invention and can be combined with them to form a blend. The complementary fat will generally comprise different fatty acids or derivatives therefrom from those specified for the composition and mixture, although they may be the same in certain embodiments of the invention.

The blend preferably comprises 5 to 80 wt. % based on the total weight of the blend, preferably 20 to 70 wt. %, of the composition according to the invention and 20 to 95 wt. %, preferably 30 to 80 wt. % of the complementary fat.

The complementary fat may be any suitable fat component having the specified $N_{20}$ value. The complementary fat is preferably selected from: cocoa butter equivalents, cocoa butter, palm oil or fractions thereof, palm kernel oil or fractions thereof, interesterified mixtures of said fats or fractions or hardened components thereof; or from liquid oil, such as sunflower oil, high oleic sunflower oil, soya bean oil, rapeseed oil, cottonseed oil, safflower oil, high oleic safflower oil, maize oil or MCT oils; and mixtures of said liquid oils and fats.

The composition, mixture or blend of the invention may be for administration in the form of an emulsion, paste or gel. The emulsion, paste or gel may, for example, contribute to masking of the off-notes associated with SECO or a derivative thereof. An emulsion base according to the invention may comprise water (preferably in an amount of 0.1 to 80 wt. %), DHA and/or EPA and/or GLA (preferably in the amounts as defined above, more preferably in about 20 to 50 wt. % based on the fat phase), a phospholipid emulsifier (preferably in the amount as defined above and including the preferred emulsifiers indicated above), and optionally, one or more of glycerol, a sweetener, such as sorbitol, flavouring, gums, and an antioxidant, such as a blend of tocopherols, dadex and rosemary.

A typical serving size of the emulsion may be, for example, 1 tablespoon (about 1 to 5 ml).

The foodstuff of the invention may be any suitable foodstuff that comprises a fat phase. However, the foodstuff is preferably selected from the group consisting of spreads, margarine, cream alternative, infant food, chocolate, confectionery, bakery products, sauces, ice-creams, ice-cream coatings, cheese, soups, mayonnaise, dressings, enteral or parental products, medical foods or foods for use in medicine.

The food supplement is preferably in the form of a soft gel or a hard capsule comprising: an encapsulating material, preferably selected from the group consisting of beeswax, gelatine, starch, modified starch, starch derivatives such as glucose, sucrose, lactose and fructose and cellulose. The food supplement may further comprise a flavouring agent. The flavouring agent may be any known flavour, such as, for example, strawberry, raspberry, lemon, mint, blackcurrant, cinnamon bark essential oil, or peppermint.

The invention also relates to the use of the composition, the mixture, the blend, the foodstuff or food supplement, or mixtures thereof according to the invention in the manufacture of a product for preventing or treating PMS, in a human, or of treating or ameliorating the symptoms of PMS in a human.

Premenstrual syndrome (PMS) is also known as premenstrual tension (PMT) and is a mixture of physical and emotional symptoms that some women experience in the days, sometimes weeks, leading up to their menstrual period.

Some of the symptoms of PMS include: headache; feeling bloated; weight gain; breast tenderness; back or lower abdominal pain; irritability or aggression; depression and anxiety; mood swings; tiredness; and poor concentration. The symptoms treated or ameliorated by the composition, mixture, blend, foodstuff or food supplement of the invention may comprise one or more of these symptoms.

In a further aspect, the invention also relates to the use of the composition, the mixture, the blend, or the foodstuff, or food supplement, or mixtures thereof according to the invention, preferably without the proviso, in the manufacture of a product for preventing or treating a prostate condition, in a human patient, or of treating or ameliorating the symptoms of a prostate condition in a human patient.

Common prostate conditions include prostatitis (inflammation of the prostate gland). Symptoms of prostatitis include painful, burning or frequent urination, weak urine flow or incomplete emptying, fever and chills, and low back pain. Other examples of prostate conditions include benign prostatic hyperplasia (BPH) (a normal, gradual enlargement of the prostate caused by hormonal effects) and prostate cancer. The symptoms of BPH include: having to wait for the urine stream to start; poor urinary flow and a variable flow rate; frequent urination; difficulty postponing urination (urgency); dribbling of urine at the end of urination. In an embodiment of the invention, the symptoms of prostate conditions that are treated or ameliorated include one or more of those listed above.

In a preferred embodiment of the invention, the prostate condition is prostate cancer.

In order to obtain health benefits, the composition, mixture, blend, foodstuff or food supplement contains an effective amount of each of EPA, DHA, GLA, and/or SECO or a derivative thereof. In particular, the effective daily amount of each may be from 10 to 100%, preferably from 25 to 85% or 200% of the recommended daily amount of EPA, DHA, GLA and/or SECO or a derivative thereof.

Examples of typical amounts of each of EPA, DHA, GLA and/or SECO or a derivative thereof are from 10 mg to 500 mg/day, preferably from 45 mg to 100 mg/day. These amounts for each of EPA, DHA, GLA and/or SECO or a derivative thereof may be considered as the recommended daily amount.

The effective amount may be less or more than the recommended daily amount and is that which produces an observable effect. A daily dosage of each of EPA, DHA, GLA and/or SECO or a derivative thereof, such as SDG, may be from 0.1 to 30 mg/kg body weight, preferably from 1 to 20 mg/kg, most preferably from 5 to 10 mg/kg body weight.

The effective amount may be delivered in a single daily portion (or a serving) of the composition, mixture, blend or foodstuff or food supplement or may be delivered in several portions, spread over a day or more than one day, such as two, three or four days.

In another aspect, the invention relates to the use of secoisolariciresinol (SECO) or a derivative thereof to improve the stability and/or sensory properties and/or nutritional activity of: a ω-3 and/or a ω-6 fatty acid, or derivatives thereof; or a composition comprising said fatty acids in a fat phase, such as for example an oil blend. Preferred oil blends include borage oil and/or fish oil.

In one embodiment of the invention, the ω-3 and/or ω-6 fatty acid is selected from one or more of EPA. DHA and GLA.

Optionally, the SECO or a derivative thereof is used in combination with lecithin. Lecithin can synergistically increase the stability of compositions comprising a ω-3 and/or a ω-6 fatty acid in combination with SECO or a derivative thereof.

It is preferred that the derivative of SECO is secoisolariciresinol diglucoside (SDG) although other derivatives could be used.

In a particularly preferred embodiment of the invention, the composition is a food supplement.

Other components typically used in the formulation of fat compositions may be included in the compositions of the invention, preferably in an amount of from 0.001 to 20 wt. %, more preferably from 0.01 to 5 wt. %. Such components may include flavouring agents, thickeners, such as gelatine, for example, porcine gelatin, colouring agents (e.g., carob colour), glycerine, buffers, salts, acids, such as citric acid, chelating agents, such as EDTA, fillers, sugars, such as glucose, fructose and sucrose, sweeteners, such as stevia extract and/or citrus extracts, and bulking agents such as silica.

The compositions of the invention preferably comprise water in an amount of from 0.001 wt. % to 50 wt. %, more preferably from 0.01 to 10 wt. % by weight of the composition.

The composition, mixture or blend of the invention may be packaged in the form of a bottle, such as a plastic or glass bottle, or a single dose sachet.

The listing or discussion of an apparently prior-published document in this specification should not necessarily be taken as an acknowledgement that the document is part of the state of the art or is common general knowledge.

The following non-limiting examples illustrate the invention and do not limit its scope in any way. In the examples and throughout this specification, all percentages, parts and ratios are by weight unless indicated otherwise.

EXAMPLES

The SDG used in the examples was Linumlife™ Extra (LLE) (Standardized Flax Lignan), available from Acatris. An AOM method was used on the Rancimat 743 model. The AOM method was the AOM automated method of AOCS Cd 12-57.

The fish oil used was 1812TG, available from Bioriginal and comprises EPA and DHA. The weight ratio of EPA to DHA is about 1.6:1.

The borage oil (23% GLA-GMO free) was obtained from Bioriginal and comprises 23 wt. % GLA.

The antioxidant used was DADEX® 259 (Dadex org), obtained from Acatris, in an amount of 0.2 wt. % based on the weight of the composition.

The lecithin used was lesoy unbleached lecithin, fcc obtained from Acatris.

Example 1

Samples of borage oil, fish oil and a mixture of borage oil and fish oil were combined with an antioxidant.

The stability of the samples was measured using the Rancimat method on a Rancimat apparatus (available from Metrohm) at 98° C. with and without SDG to investigate the effect of SDG on the stability of EPA, DHA and GLA.

The results are set out in Table 1. The figures for the oils indicate the time taken for decomposition in the absence and the presence of SDG. Since the stability is higher for borage oil in the presence of SDG (i.e., the borage oil takes longer to decompose), this data shows that SDG can improve the stability of GLA.

The data for fish oil (EPA and DHA) shows a trend of increasing stability with increasing amounts of SDG, while the data for a mixture of borage oil and fish oil is consistent with that for borage oil alone.

All oils showed an increase in stability with an increasing concentration of SDG/g oil. A particularly high increase in stability was found for the blend of fish oil (1812TG) and borage oil.

Additional trials were conducted on the fish oil blends at a lower rancimat temperature of 80° C. since typical AOM temperatures of 98° C. are quite high for sensitive oils. However, no significant differences in the trends were noted at the reduced operating temperature.

TABLE 1

|  | AOM @98° C. (Rancimat hrs) | | |
| --- | --- | --- | --- |
| SDG (mg/g Oil) | Borage Oil (23% GLA) with Anti Oxidant | Fish Oil (1812TG) with Anti Oxidant | Borage Oil: Fish Oil (50:50) with Anti Oxidant |
| 0 | 17.73 | 1.33 | 2.61 |
| 0.73 | 17.94 | 1.40 | 4.85 |
| 2.15 | 19.67 | 1.38 | 5.92 |
| 3.58 | 20.06 | 1.55 | 6.43 |

Example 2

Experiments were conducted to determine the affect on the stability of selected oils with varying concentrations of SDG.

Determinations were made by measuring the resistance to oxidation by rancimat (AOM) as indicated above in Example 1.

In the experiments, typical dosage quantities of SDG per serving were used. A recommended serving size of Borage oil or Fish oil may be 4.7 g. Therefore 2.12 mg/g SDG calculates to 10 mg SDG/4.7 g serving and 6.38 mg/g SDG calculates to 30 mg SDG/4.7 g serving. A similar stability increase to that shown in Example 1 can also be seen when samples were formulated to serving size dosages, as shown in Table 2.

TABLE 2

| SDG (m/g Oil) | AOM @98° C. (Rancimat hrs) | | |
| --- | --- | --- | --- |
| | Borage Oil (23% GLA) with Anti Oxidant | Fish Oil (1812TG) with Anti Oxidant | Borage Oil: Fish Oil (50:50) with Anti Oxidant |
| 0 | 17.73 | 1.33 | 2.61 |
| 2.12 | 18.14 | 1.25 | 5.52 |
| 6.38 | 19.35 | 3.09 | 6.89 |

Example 3

Additional experiments were conducted in which the composition also comprised lecithin. The data shown in Table 3 indicates that the presence of lecithin with SDG can synergistically enhance the stability of the oil blends.

TABLE 3

| SDG (mg/g Oil) | AOM @98° C. (Rancimat hrs) | | |
| --- | --- | --- | --- |
| | Borage Oil (23% GLA) with Anti Oxidant | Fish Oil (1812TG) with Anti Oxidant | Borage Oil: Fish Oil (50:50) with Anti Oxidant |
| 0 mg SDG (+0 mg Lecithin) | 16.32 | 1.23 | 2.7 |
| 2.12 mg SDG (+7.4 mg Lecithin) | 26.29 | 2.73 | 13.61 |
| 6.38 mg SDG (+18.1 mg Lecithin) | 34.30 | 11.15 | 19.87 |
| 10.6 mg SDG (+21.3 mg Lecithin) | 38.87 | 13.77 | 24.28 |

Example 4

A capsule according to the invention may comprise

| EPA or DHA or GLA | 550 mg |
| --- | --- |
| SDG | 10-50 mg |
| Beeswax | 150 mg |
| Lecithin | 34 to 100 mg |
| Others (including flavouring) | to 1000 mg |

Example 5

A single serving from a bottled liquid product according to the invention may comprise

| EPA or DHA or GLA | 550 mg |
| --- | --- |
| SDG | 10-50 mg |
| Lecithin | 34-100 mg |
| Others (including flavouring) | to 1000 mg |

Example 6

Experiments were carried out to determine the increased stability of selected oils with varying concentrations of SDG from Linumlife Extra (Standardized Flax Lignan), lecithin and antioxidant.

Protocol: Determinations were made by measuring the resistance to oxidation by rancimat (automated AOM).

Oils: Borage Oil (23 wt. % GLA)
Fish Oil (18 wt. % EPA, 12 wt. % DHA)

Additives: Linumlife extra (LLE)
Soy Lecithin
Dadex RM (antioxidant), which has the following composition:

| Rosemary extract | 10% |
| --- | --- |
| Mixed Tocopherols | 5% |
| Citric Acid | 5% |
| Ascorbyl Palmitate | 5% |
| Carrier | |
| Propylene Glycol | 75% |

The blends evaluated here have been formulated to liquid dosage form. The active levels chosen provide 10 mg, 30 mg and 50 mg SDG/tsp serving.

| Dosage | | | |
| --- | --- | --- | --- |
| mg SDG/g oil | 2.17 | 6.38 | 10.6 |
| mg SDG/1 tsp oil | 10 | 30 | 50 |

Ratio of Linumlife to lecithin used;

| Additive: | % w/w | | |
| --- | --- | --- | --- |
| Linumlife Extra: | 1.09 | 3.20 | 5.32 |
| Lecithin | 0.75 | 1.80 | 2.13 |

Figure 4:
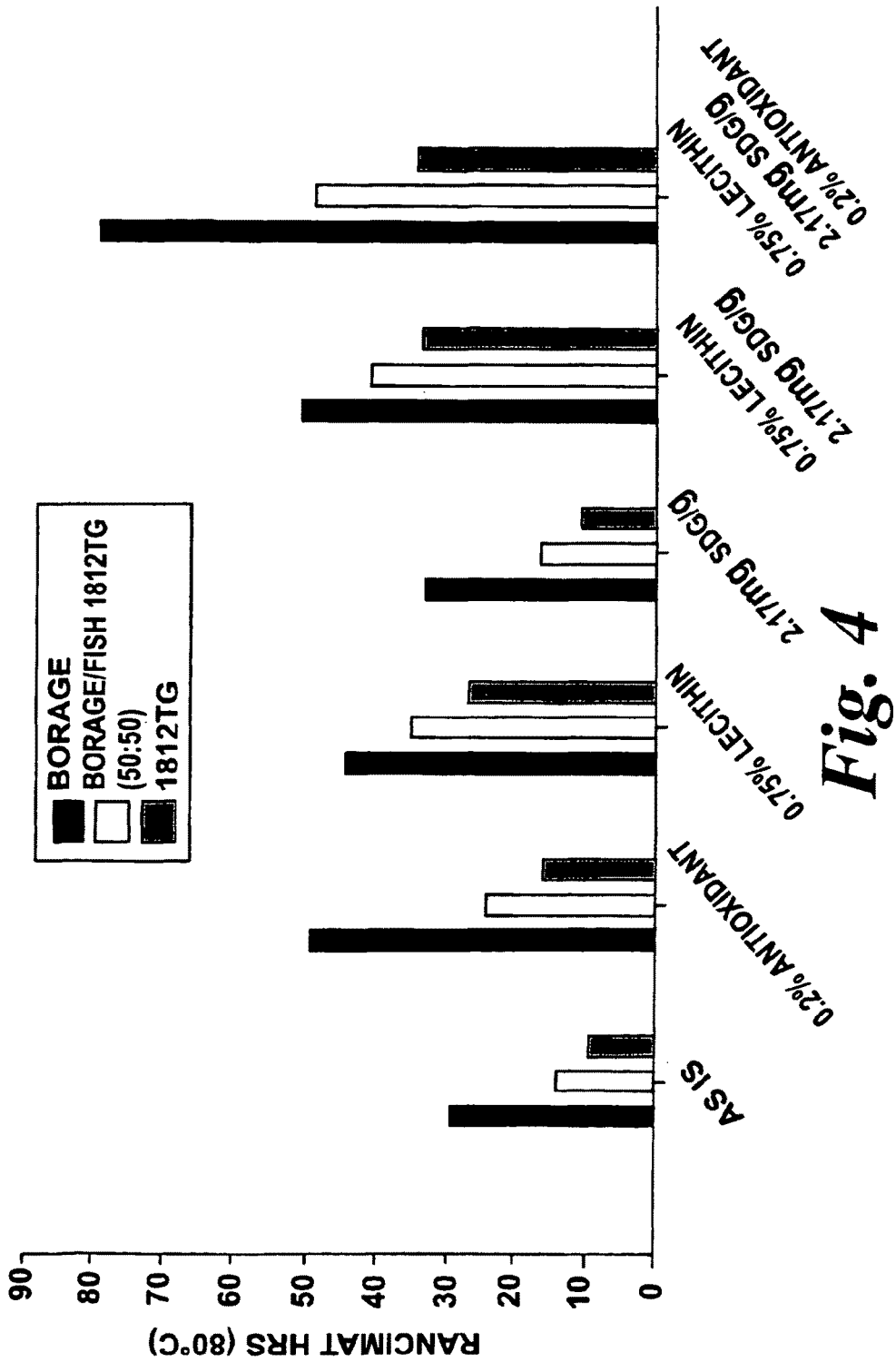
FIG. 4 shows the resistance to oxidation by addition of single and combination antioxidants for 10 mg SDG/tsp dosage.
Figure 5:
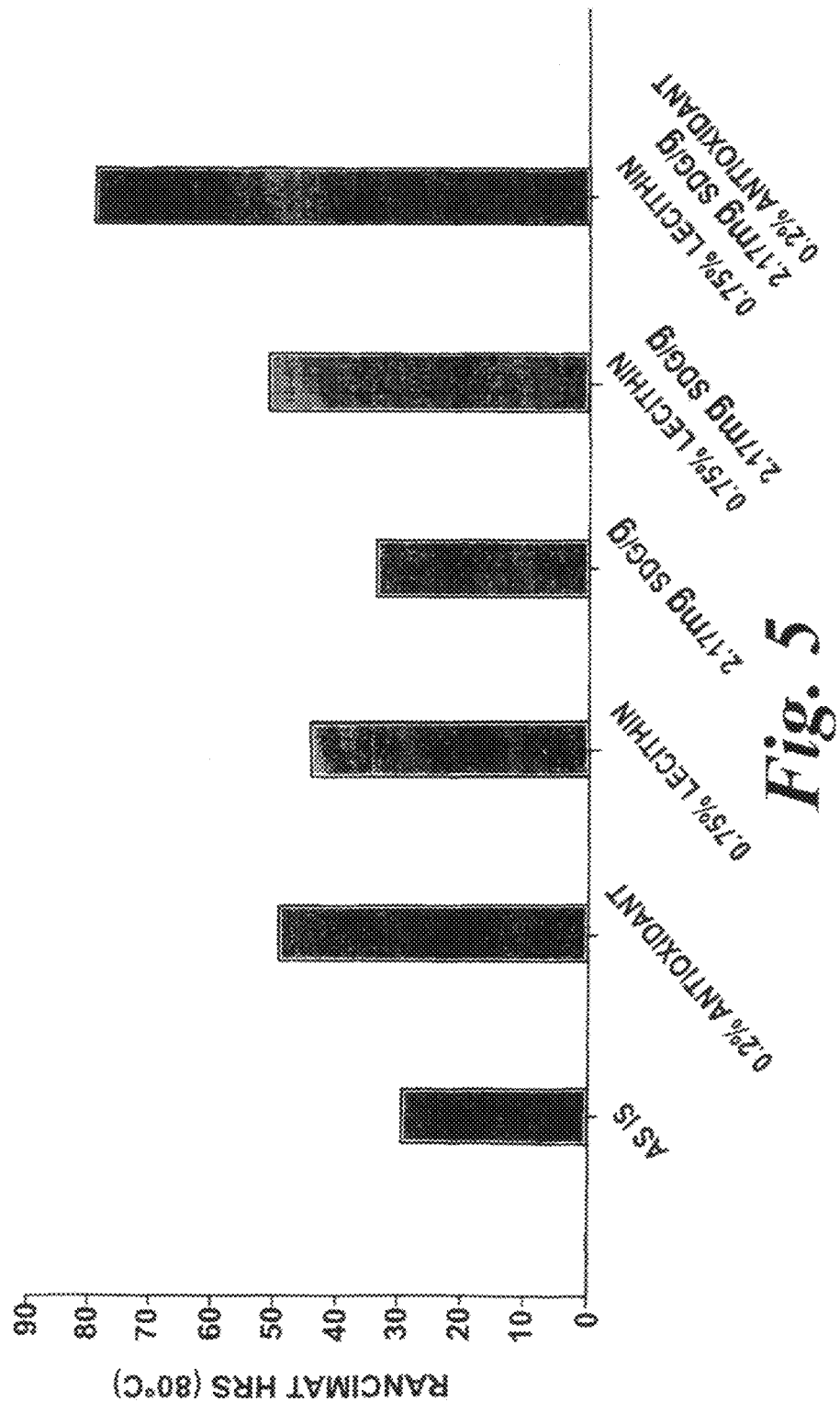
FIG. 5 shows the resistance to oxidation by addition of single and combination antioxidants in borage oil.
Figure 6:
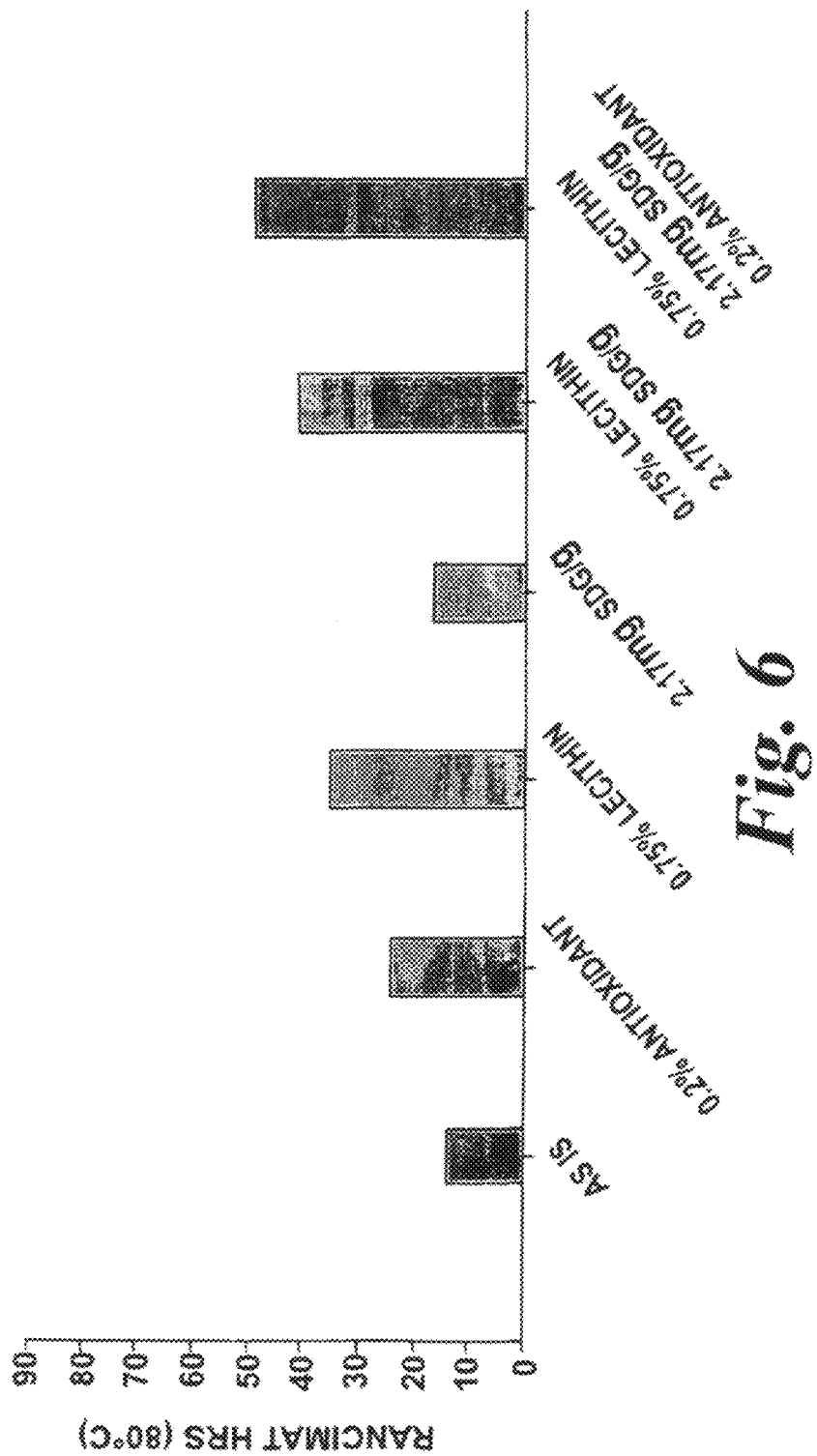
FIG. 6 shows the resistance to oxidation by addition of single and combination antioxidants in a borage and fish oil blend.
Figure 7:
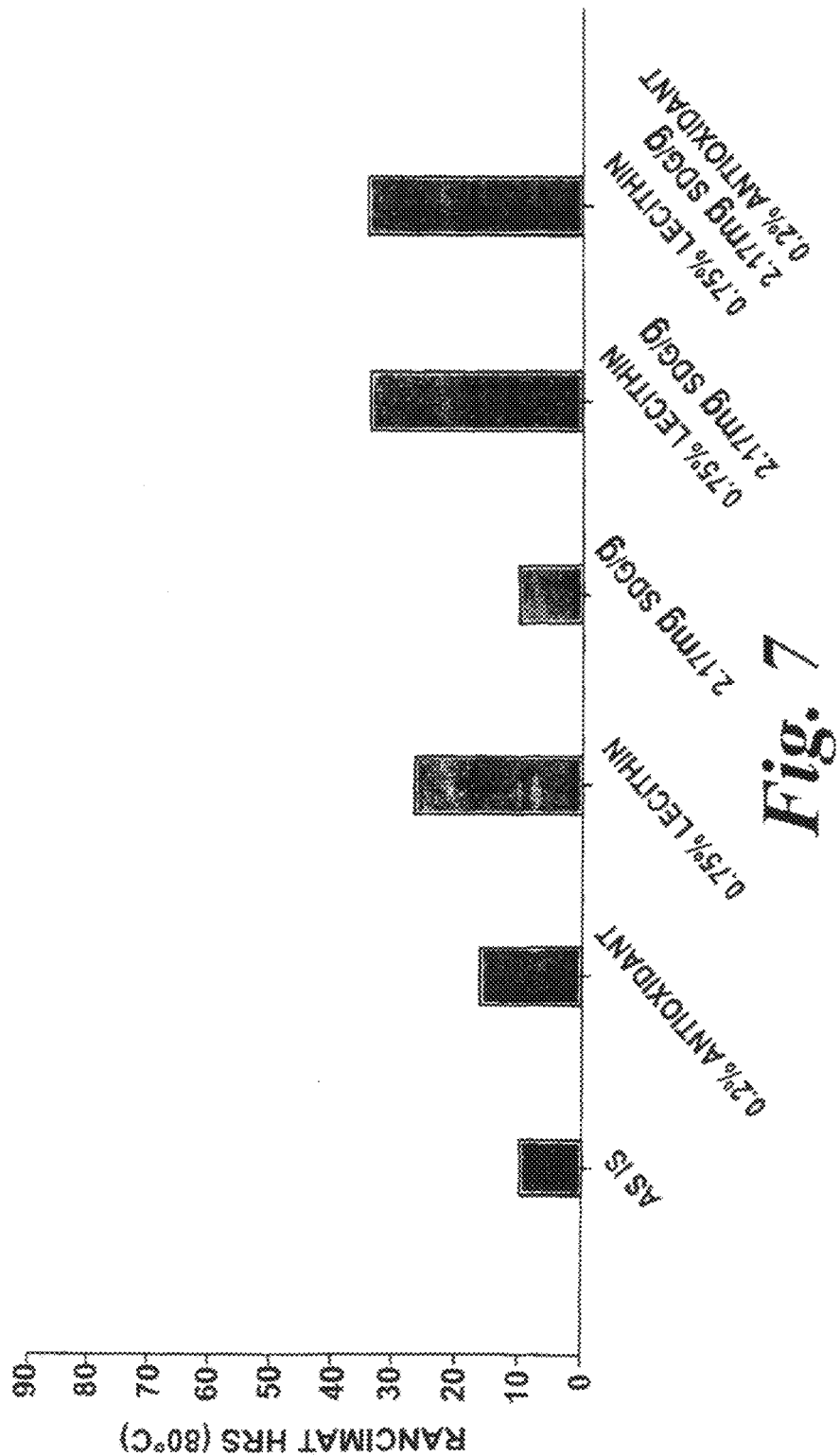
FIG. 7 shows the resistance to oxidation by addition of single and combination antioxidants in fish oil.

Evaluation:

Table 4 contains rancimat results for each oil type evaluated as single oils and with the addition of each single ingredient based on the formulation ratios above. This data is also shown in the form of a graph in FIG. 4.

TABLE 4

| Test sample | usage rate | Active: mg SDG/g blend | Rancimat hrs (80° C.) | | |
| --- | --- | --- | --- | --- | --- |
| | | | Borage Oil (23%) | Fish Oil 1812TG | Borage/ 1812TG (50:50) |
| As is | — | N/A | 29.58 | 9.70 | 13.99 |
| Dadex RM | 0.20% | N/A | 49.67 | 16.36 | 24.53 |
| Lecithin (Unbleached) | 0.75% | N/A | 44.71 | 27.12 | 35.53 |
| Lecithin (Unbleached) | 1.80% | N/A | 71.35 | 21.64 | 23.60 |
| Lecithin (Unbleached) | 2.13% | N/A | 83.91 | 27.35 | 41.98 |
| LLE (Flax) | 1.09% | 2.17 | 33.60 | 10.87 | 16.59 |
| LLE (Flax) | 3.20% | 6.38 | 34.76 | 9.00 | 15.44 |

10 mg SDG/tsp Dosage

Tables 5 and 6 show the rancimat results for blends prepared using the above mentioned ratios of Linumlife to lecithin, with and without the addition of antioxidant, for 10 mg SDG/tsp dosage.

TABLE 5

| Test sample | usage rate | Active mg SDG/g blend | Rancimat hrs (80° C.) Borage Oil (23%) | Fish Oil 1812TG | Borage/ 1812TG (50:50) |
|---|---|---|---|---|---|
| As is | — | N/A | 29.58 | 9.7 | 13.99 |
| Dadex RM | 0.20% | N/A | | | |
| Lecithin (Unbleached) | 0.75% | N/A | | | |
| LLE (Flax) | 1.09% | 2.17 | 79.58 | 34.69 | 49.22 |

TABLE 6

| Test sample | usage rate | Active mg SDG/g blend | Rancimat hrs (80° C.) Borage Oil (23%) | Fish Oil 1812TG | Borage/ 1812TG (50:50) |
|---|---|---|---|---|---|
| As is | — | N/A | 29.58 | 9.7 | 13.99 |
| Lecithin (Unbleached) | 0.75% | N/A | | | |
| LLE (Flax) | 1.09% | 2.17 | 51.1 | 34.23 | 41.47 |

The data in Tables 5 and 6 is also shown in the form of graphs in FIGS. 4 to 7.

30 mg SDG/tsp Dosage

Figure 8:
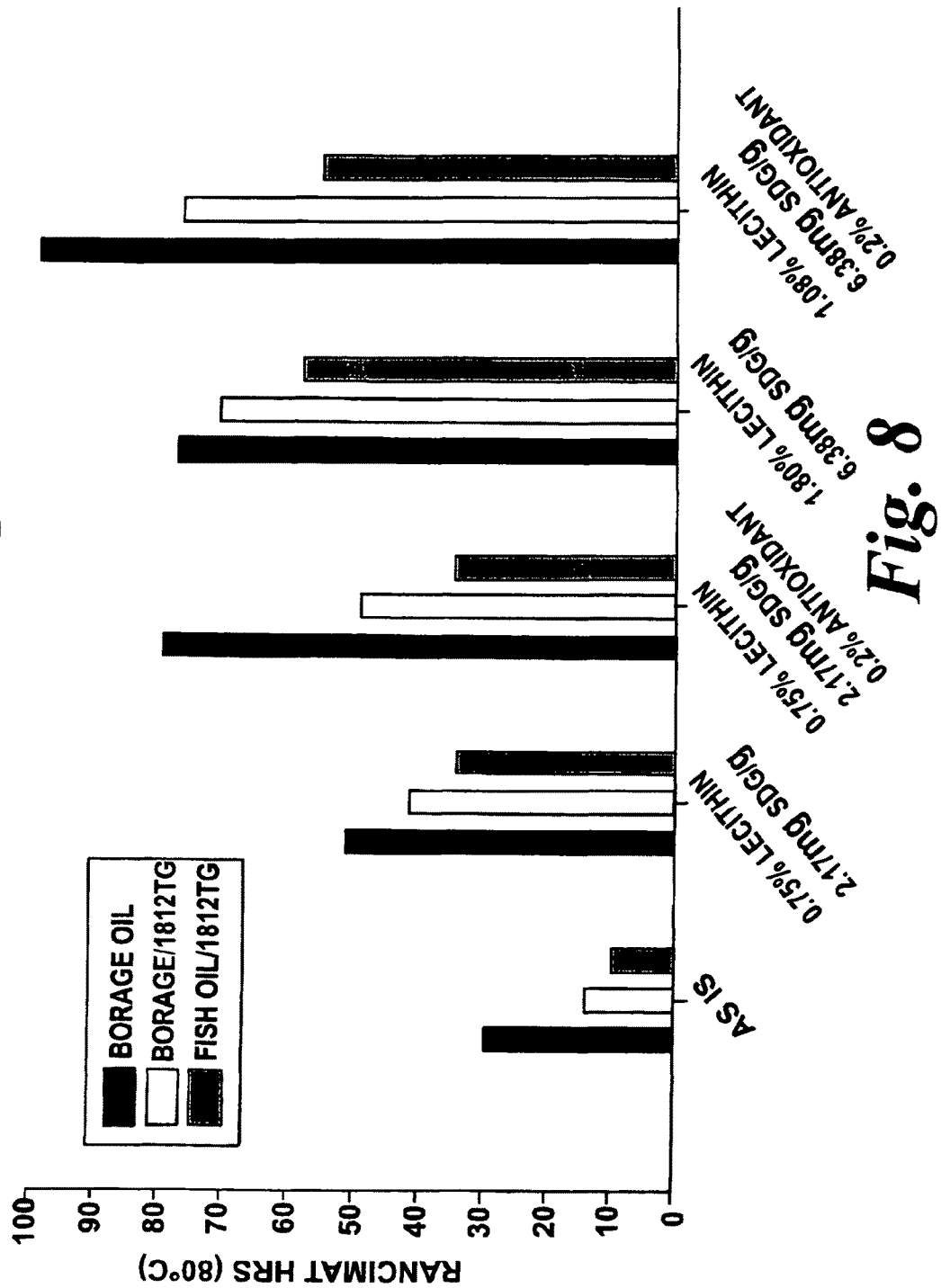
FIG. 8 shows the resistance to oxidation by addition of combination antioxidants in a variety of oil types for 30 mg SDG/tsp dosage.

Tables 7 and 8 and FIG. 8 show the rancimat results for blends prepared using the above mentioned ratios of Linumlife to lecithin, with and without the addition of antioxidant, for 30 mg SDG/tsp dosage.

TABLE 7

| Test sample | usage rate | Active mg SDG/g blend | Rancimat hrs (80° C.) Borage Oil (23%) | Fish Oil 1812TG | Borage/ 1812TG (50:50) |
|---|---|---|---|---|---|
| As is | — | N/A | 29.58 | 9.7 | 13.99 |
| Dadex RM | 0.20% | N/A | | | |
| Lecithin (Unbleached) | 1.80% | N/A | | | |
| LLE (Flax) | 3.20% | 6.38 | 99.0 | 55.27 | 76.61 |

TABLE 8

| Test sample | usage rate | Active mg SDG/g blend | Borage Oil (23%) | Fish Oil 1812TG | Borage/ 1812TG (50:50) |
|---|---|---|---|---|---|
| As is | — | N/A | 29.58 | 9.7 | 13.99 |
| Lecithin (Unbleached) | 1.80% | N/A | | | |
| LLE (Flax) | 3.20% | 6.38 | 77.3 | 58.17 | 70.87 |

50 mg SDG/tsp Dosage

Figure 9:
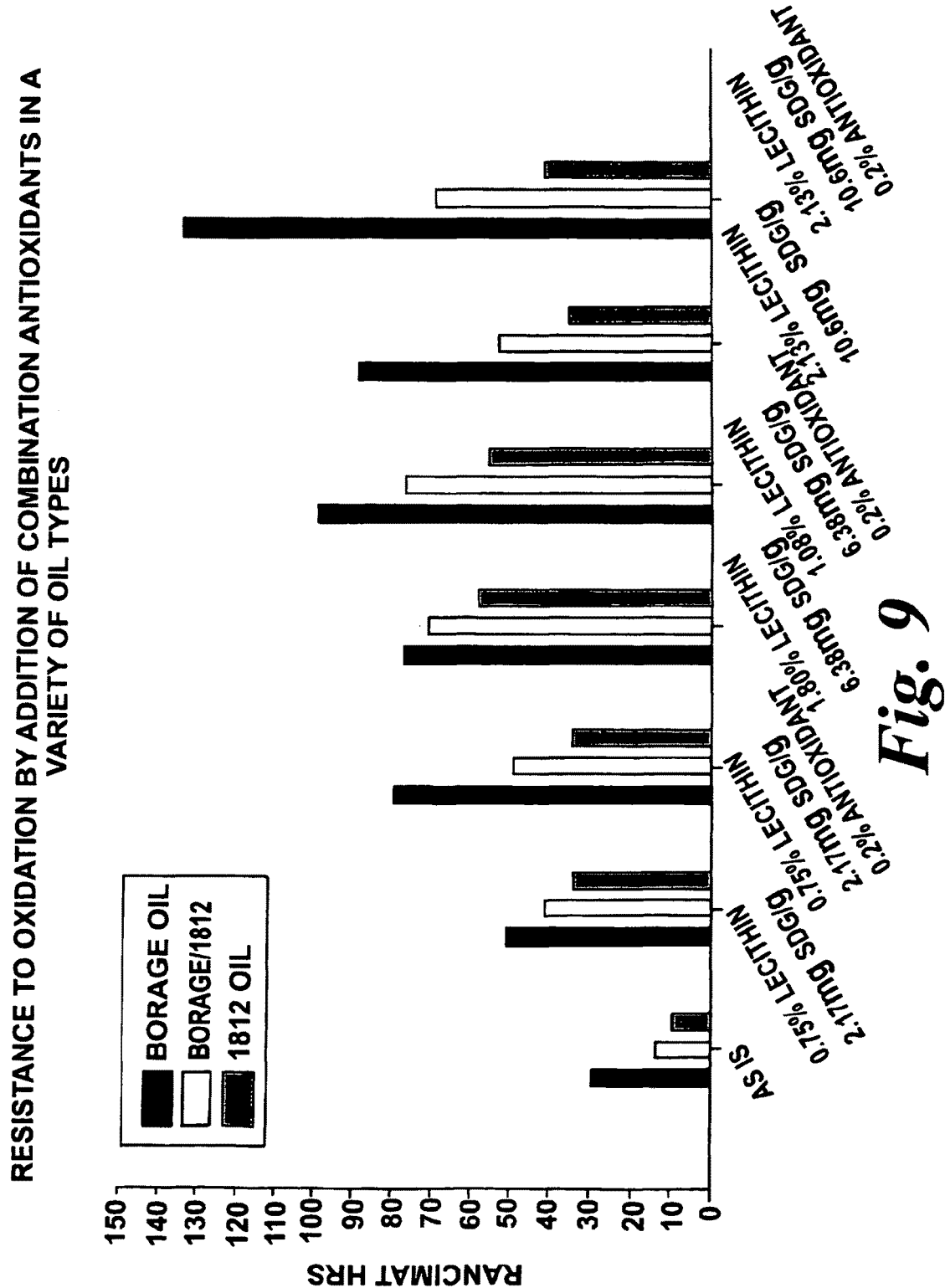
FIG. 9 shows the resistance to oxidation by addition of combination antioxidants in a variety of oil types for 50 mg SDG/tsp dosage.

Tables 9 and 10 and FIG. 9 show the rancimat results for blends prepared using the above mentioned ratios of Linumlife to lecithin, with and without the addition of antioxidant, for 50 mg SDG/tsp dosage.

TABLE 9

| Test sample | usage rate | Active mg SDG/g blend | Rancimat hrs (80° C.) Borage Oil (23%) | Fish Oil 1812TG | Borage/ 1812TG (50:50) |
|---|---|---|---|---|---|
| As is | — | N/A | 29.58 | 9.7 | 13.99 |
| Dadex RM | 0.20% | N/A | | | |
| Lecithin (Unbleached) | 2.13% | N/A | | | |
| LLE (Flax) | 5.32% | 10.6 | 134.07 | 41.55 | 69.06 |

TABLE 10

| Test sample | usage rate | Active mg SDG/g blend | Borage Oil (23%) | Fish Oil 1812TG | Borage/ 1812TG (50:50) |
|---|---|---|---|---|---|
| As is | — | N/A | 29.58 | 9.7 | 13.99 |
| Lecithin (Unbleached) | 2.13% | N/A | | | |
| LLE (Flax) | 5.32% | 10.6 | 88.74 | 34.78 | 52.74 |

Example 7

Evaluation of Alternative Sources of Lecithin and Antioxidants:

Further experiments were done to evaluate other antioxidant and lecithin sources.

Figure 10:
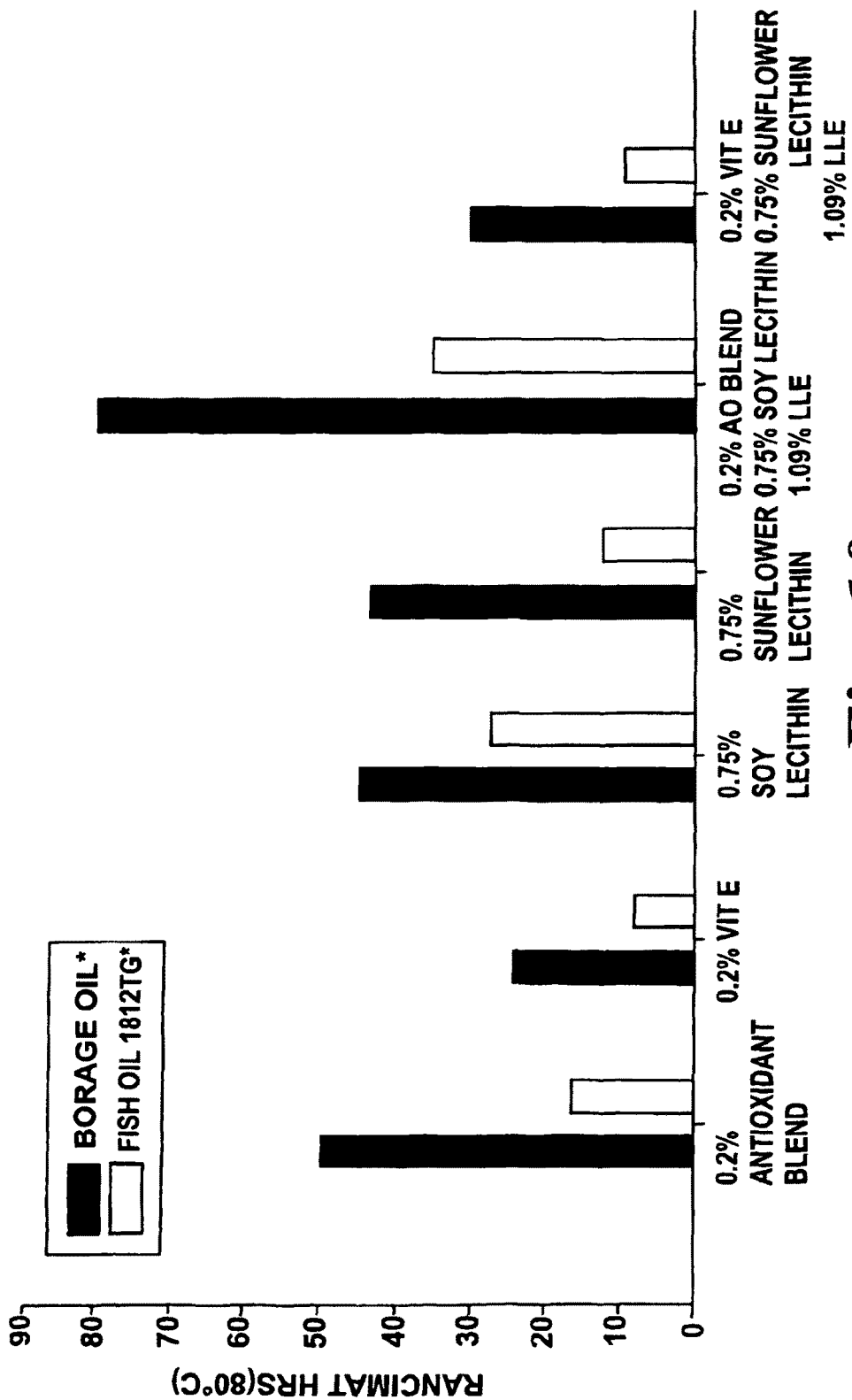
FIG. 10 shows a comparison of alternative antioxidants and combined antioxidant additives as measured by resistance to oxidation by rancimat.

Rancimat analysis, as described above, was performed on oils with single additions of each alternative source of lecithin (Soy or Sunflower) and antioxidant (Dadex RM or Vitamin E). Formulation blends with both alternative additives were also measured. Results are presented below in FIG. 10.

| | | Borage Oil (23%) | Fish Oil 1812TG |
|---|---|---|---|
| Dadex RM | 0.20% | 49.67 | 16.36 |
| DAT (Vit E) | 0.20% | | 7.97 |
| Soy Lecithin (unbleached) | 0.75% | 44.71 | 27.12 |
| Sunflower Lecithin | 0.75% | | 11.87 |

There is a further synergistic increase in stabilisation provided by the combination of soy lecithin with the antioxidant blend Dadex RM and Linumlife Extra, as compared to the combination of sunflower lecithin, vitamin E and Linumlife. This is seen with both oil types.

In comparing the alternative lecithin and antioxidant sources, vitamin E shows less resistance to oxidation as compared to the Dadex RM antioxidant blend when used at equal addition rates of 0.2%. The sunflower lecithin provides similar rancimat hours for borage oil as compared to soy lecithin but fish oil 1812TG is less stable with the addition of sunflower lecithin as compared to the same 0.75% usage rate of soy lecithin.

The formulation prepared using sunflower lecithin, vitamin E and Linumlife Extra shows a slight increase in antioxidant activity over addition of vitamin E alone. However this combination shows a moderate decrease in antioxidant activity from sunflower lecithin alone.

Example 8

Further experiments were conducted to compare flax lignan to other lignan sources, such as sesame and spruce. Table 13 includes the specifications for the following lignan materials: HMRlignan (Norwegian Spruce Lignans): Linnea Inc; Sesamin (Sesame Lignans): Nanjing depont Pharmechem; and Linumlife Extra (Flax Lignans): Frutarom.

The following lignan formulations were tested in the specified amounts:
(i) Flax Lignan (Linumlife Extra 20% SDG), 3.20% usage rate=6.38 mg SDG/g blend.
(ii) Sesame lignan (50% Active), 1.28% usage rate=6.38 mg Active/g blend.
(iii) Spruce Lignan (HMR lignan 90% Active), 0.71% usage rate=6.38 mg Active/g blend.

Rancimat Results:

Lignan Only:

TABLE 11

| | | AOM (80° C.) hrs | | |
| --- | --- | --- | --- | --- |
| Oil | Active Lignan ~ mg Active/g blend | Flax Lignan (20%) | Sesame Lignan (50%) | Spruce Lignan* (90%) |
| Borage (23% GLA) | 6.38 | 36.03 | 37.71 | 37.13 |
| Borage/Fish 1821TG (50:50) | 6.38 | 15.82 | 16.39 | 45.55 |
| Fish 1812TG | 6.38 | 10.12 | 10.97 | 39.11 |

Figure 11:
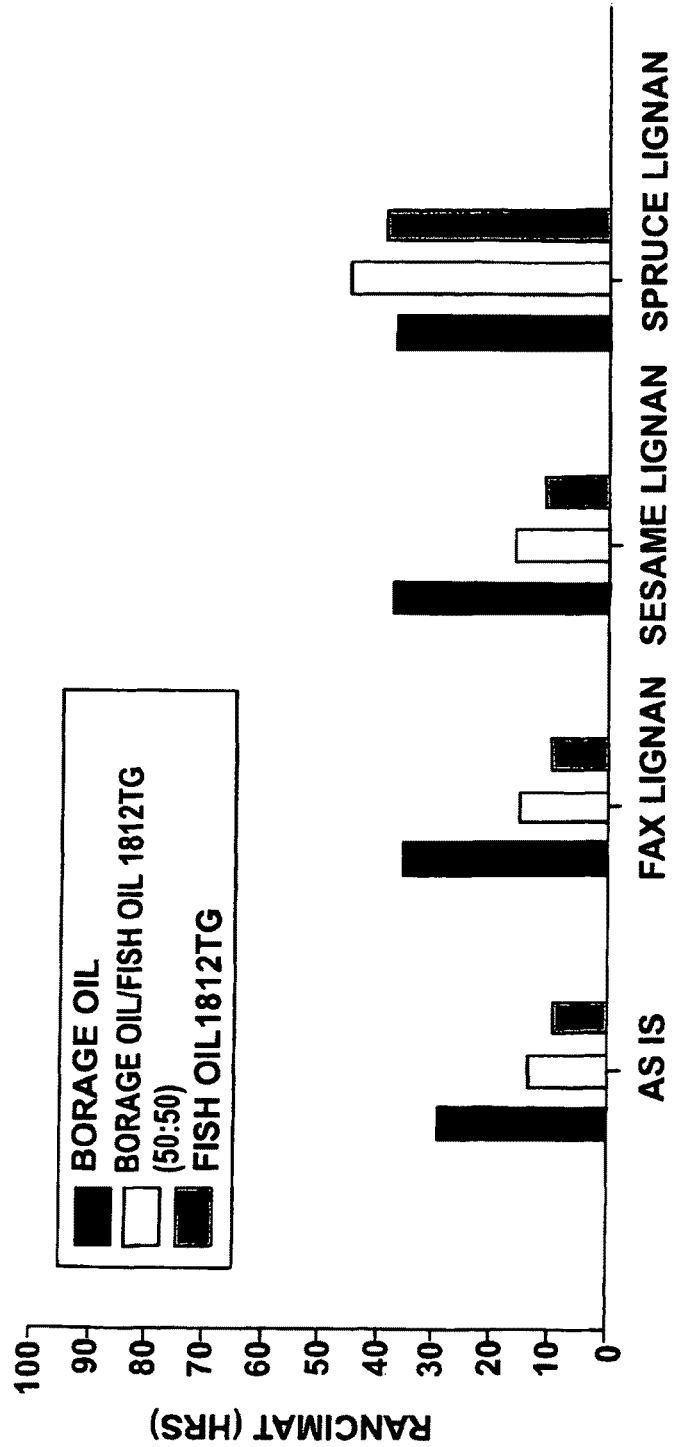
FIG. 11 shows a comparison of resistance to oxidation for combinations of oils and various lignan sources at 6.38 mg lignan/g.

*The samples containing spruce Lignans did not provide stable rancimat readings. The instrument graphs were very noisy making the end point determination very difficult. These samples were retested after high shearing of the blend to reduce particle size and this did allow for more stable readings on the rancimat. The results are also shown in FIG. 11.

Lignan with Lecithin:

TABLE 12

| | | Active | AOM (80° C.) hrs | | |
| --- | --- | --- | --- | --- | --- |
| Oil | % Lecithin | Lignan ~mg Active/g blend | Flax Lignan (20%) | Sesame Lignan (50%) | Spruce Lignan (90%) |
| Borage (23% GLA) | 1.80 | 6.38 | 86.93 | 70.17 | 118.97 |
| Borage/Fish 1821TG (50:50) | 1.80 | 6.38 | 70.87 | 47.53 | 65.27 |
| Fish 1812TG | 1.80 | 6.38 | 58.17 | 25.44 | 65.27 |

Figure 12:
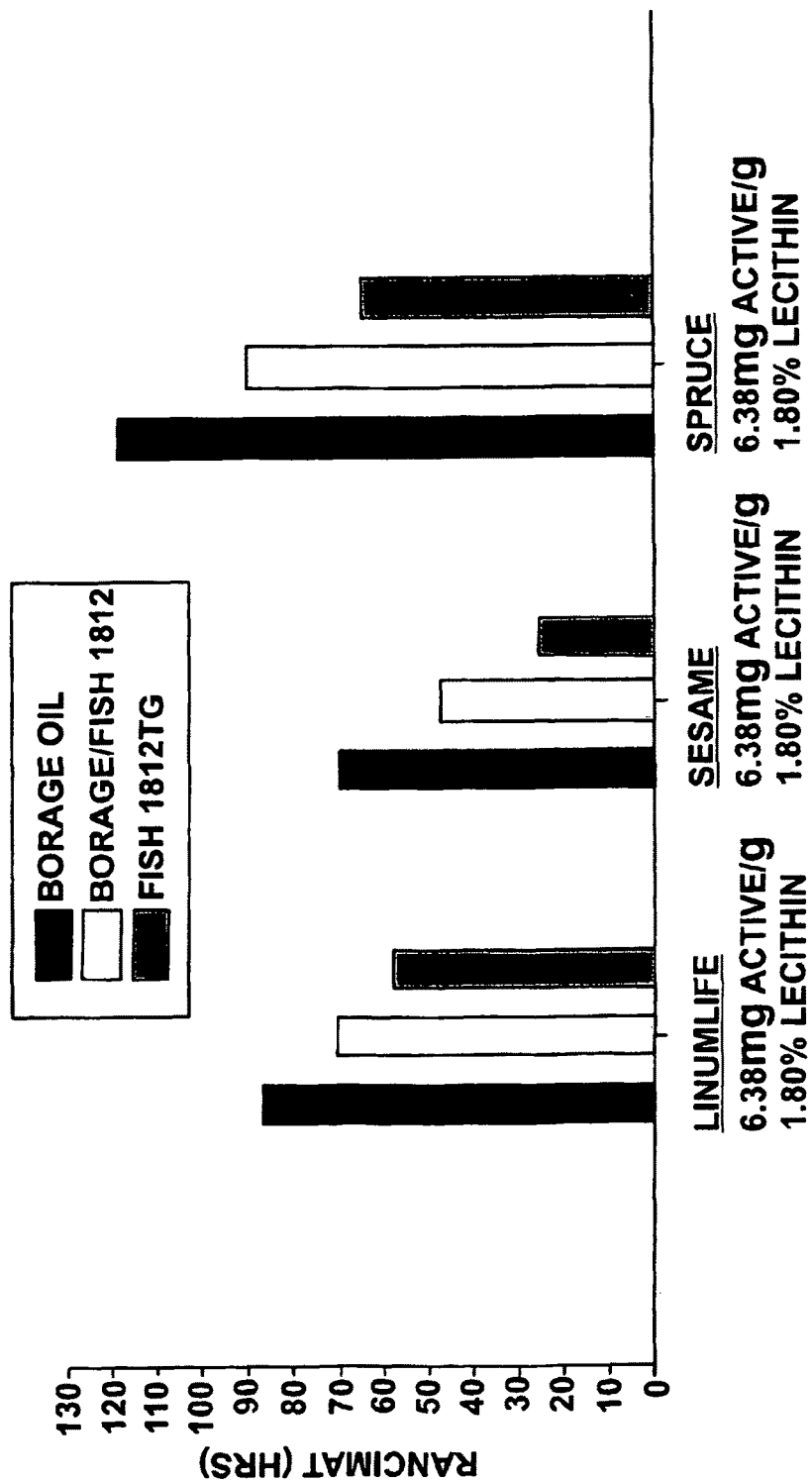
FIG. 12 shows a comparison of resistance to oxidation of various antioxidant lignan sources and lecithin.

The results are also shown in FIG. 12.

TABLE 13

| Specification Parameters | Linumlife Extra | HMRlignan | Sesamin |
| --- | --- | --- | --- |
| Plant source/Plant part | Flax seed Hulls | Spruce *Picea Abies* (Knot wood) | Sesame *Sasamum indicum* DC |
| Assay | SDG | Hydroxymatairesinol Potassium acetate | Cis-4-hydroxy-L-proline |
| Assay % | NLT* 200 mg/g (20%) | NLT 90% | NLT 50% |
| Related substances | | Matairesinols (NMT 7%) | |
| Carrier | Potato maltodextrin | §NR | NR |
| Appearance | Beige - Brown powder | Off with free flowing granulate | White crystalline powder |
| Solubility | | Soluble in methanol | |
| Water content % | NMT◻ 5% | NMT 10% | NMT 0.5% |
| Heavy metals | NMT 5 ppm | NMT 20 ppm | NMT 10 ppm |
| Residual solvents | Ethanol (NMT 5,000 mg/kg) | Ethanol (NMT 1.0%) Ethyl Acetate (NMT 0.5%) | NR |
| Tapped density g/ml | 0.45-0.75 g/ml | 0.7 g/ml | NR |
| Micro (Total plate count) | <10,000 cfu/g | <1000 cfu/g | <1000 cfu/g |
| Fungus (yeast & mold) | <1000 cfu/g | <100 cfu/g | <100 cfu/g |

*NTL: not less than
◻NMT: not more than
§NR: not reported

Example 9

An internal taste panel was also conducted to evaluate the sensory acceptability of the three lignan sources evaluated.

Taste Comparison (Lignan Sources): Blends were prepared to 6.38 mg active per gram blend in borage oil and the taste compared. Sensory evaluations were conducted with a 5 person taste panel and the results are tabulated below.

| | | Overall | Negative Flavor Characteristics | | | |
| --- | --- | --- | --- | --- | --- | --- |
| Lignan source | Usage rate (w/w %) | Sensory Quality | Bitter | Astringent | Acidic/ Sulfury | Chalky/ Earthy |
| Flax Lignan (20%) | 3.20% | 2.6 | 2.2 | 0.6 | 0.4 | 0.6 |
| Sesame Lignan (50%) | 1.28% | 3.6 | 0 | 0 | 0 | 0.8 |
| Spruce Lignan (90%) | 0.71% | 7.8 | 2.2 | 1.4 | 0.4 | 0.4 |

Overall sensory Quality (Scale):
10 = bland
8 = faint

-continued

| Lignan source | Usage rate (w/w %) | Overall Sensory Quality | Bitter | Astringent | Acidic/ Sulfury | Chalky/ Earthy |
|---|---|---|---|---|---|---|

5 = moderate
3 = strong
1 = extreme
Negative Flavor Characteristics (Scale):
0 = not present
1 = weak/slight
2 = moderate/definite
3 = strong The following examples, Examples 10 to 18 are all examples of suitable formulae for administration orally.

Example 10

| Formula (10 mg SDG/serving) | mg/4.7 g serving | LLE RM spec (mg/g) | mg SDG/4.7 g serving |
|---|---|---|---|
| Premix | | | |
| Borage Oil 23% | 1040.00 | 200 | 10.0 |
| Lecithin | 35.00 | | |
| Linumlife Extra (LLE) | 50.00 | | |
| Dadex Org | 10.00 | | |
| Other | | | |
| Borage Oil 23% | 3565.00 | | |
| Total | 4700.00 | | |

Example 11

| Formula (30 mg SDG/serving) | mg/4.7 g serving | LLE RM spec (mg/g) | mg SDG/4.7 g serving |
|---|---|---|---|
| Premix | | | |
| Borage Oil 23% | 1040.00 | 200 | 30.0 |
| Lecithin | 85.00 | | |
| Linumlife Extra | 150.00 | | |
| Dadex Org | 10.00 | | |
| Other | | | |
| Borage Oil 23% | 3415.00 | | |
| Total | 4700.00 | | |

Example 12

| Formula (50 mg SDG/serving) | mg/4.7 g serving | LLE RM spec (mg/g) | mg SDG/4.7 g serving |
|---|---|---|---|
| Premix | | | |
| Borage Oil 23% | 2640.00 | 200 | 50.0 |
| Lecithin | 100.00 | | |
| Linumlife Extra | 250.00 | | |
| Dadex Org | 10.00 | | |
| Other | | | |
| Borage Oil 23% | 1700.00 | | |
| Total | 4700.00 | | |

Example 13

| Formula (10 mg SDG/serving) | mg/4.7 g serving | LLE RM spec (mg/g) | mg SDG/4.7 g serving |
|---|---|---|---|
| Premix | | | |
| Borage Oil 23% | 470.00 | 200 | 10.0 |
| Fish Oil 1812TG | 470.00 | | |
| Lecithin | 35.00 | | |
| Linumlife Extra | 50.00 | | |
| Dadex Org | 10.00 | | |
| Other | | | |
| Borage Oil 23% | 1832.50 | | |
| Fish Oil 1812TG | 1832.50 | | |
| Total | 4700.00 | | |

Example 14

| Formula (30 mg SDG/serving) | mg/4.7 g serving | LLE RM spec (mg/g) | mg SDG/4.7 g serving |
|---|---|---|---|
| Premix | | | |
| Borage Oil 23% | 470.00 | 200 | 30.0 |
| Fish Oil 1812TG | 470.00 | | |
| Lecithin | 85.00 | | |
| Linumlife Extra | 150.00 | | |
| Dadex Org | 10.00 | | |
| Other | | | |
| Borage Oil 23% | 1757.50 | | |
| Fish Oil 1812TG | 1757.50 | | |
| Total | 4700.00 | | |

Example 15

| Formula (50 mg SDG/serving) | mg/4.7 g serving | LLE RM spec (mg/g) | mg SDG/4.7 g serving |
|---|---|---|---|
| Premix | | | |
| Borage Oil 23% | 470.00 | 200 | 50.0 |
| Fish Oil 1812TG | 470.00 | | |
| Lecithin | 100.00 | | |
| Linumlife Extra | 250.00 | | |
| Dadex Org | 10.00 | | |
| Other | | | |
| Borage Oil 23% | 1700.00 | | |
| Fish Oil 1812TG | 1700.00 | | |
| Total | 4700.00 | | |

Example 16

| Formula (10 mg SDG/serving) | mg/4.7 g serving | LLE RM spec (mg/g) | mg SDG/4.7 g serving |
|---|---|---|---|
| Premix | | | |
| Fish Oil 1812TG | 955.00 | 200 | 10.0 |
| Lecithin | 35.00 | | |

-continued

| Formula (10 mg SDG/serving) | mg/4.7 g serving | LLE RM spec (mg/g) | mg SDG/4.7 g serving |
|---|---|---|---|
| Linumlife Extra | 50.00 | | |
| Dadex Org | 10.00 | | |
| Other | | | |
| Fish Oil 1812TG | 3650.00 | | |
| Total | 4700.00 | | |

Example 17

| Formula (30 mg SDG/serving) | mg/4.7 g serving | LLE RM spec (mg/g) | mg SDG/4.7 g serving |
|---|---|---|---|
| Premix | | | |
| Fish Oil 1812TG | 955.00 | 200 | 30.0 |
| Lecithin | 85.00 | | |
| Linumlife Extra | 150.00 | | |
| Dadex Org | 10.00 | | |
| Other | | | |
| Fish Oil 1812TG | 3500.00 | | |
| Total | 4700.00 | | |

Example 18

| (50 mg SDG/serving) | mg/4.7 g serving | LLE RM spec (mg/g) | mg SDG/4.7 g serving |
|---|---|---|---|
| Premix | | | |
| Fish Oil 1812TG | 840.00 | 200 | 50.0 |
| Lecithin | 100.00 | | |
| Linumlife Extra | 250.00 | | |
| Dadex Org | 10.00 | | |
| Other | | | |
| Fish Oil 1812TG | 3500.00 | | |
| Total | 4700.00 | | |

The invention claimed is:

1. A composition comprising a fat phase wherin the fat phase comprises more than 10 wt.% DHA and/or EPA derivatives thereof; or more than 5 wt.% GLA or a derivative thereof; or more than 10 wt.% of GLA, EPA and /or DHA in total or derivatives thereof; an amount of at least 0.3 wt.% Lecithin.

2. The composition according to claim 1, wherein the composition comprises from 1 to 10 wt.% Lecithin.

3. The composition according to claim 1, wherein when the composition comprises GLA it is free of isoflavones.

4. The composition of claim 1, wherein the SDG is obtained as a concentrate from flaxseed or is obtained in the form of a powder.

5. The composition of claim 1, wherein the composition is in the form of a capsule or a liquid.

* * * * *

UNITED STATES PATENT AND TRADEMARK OFFICE
CERTIFICATE OF CORRECTION

PATENT NO. : 9,145,534 B2
APPLICATION NO. : 12/309787
DATED : September 29, 2015
INVENTOR(S) : Adrian Hughes, Rakesh Kapoor and Jeanette Fusick It is certified that error appears in the above-identified patent and that said Letters Patent is hereby corrected as shown below:

Claims

Column 20, Lines 18-23, Delete Claim 1 in its entirety and substitute the following:

"A composition comprising:
  (1) a fat phase comprising:
    (a) fish oil comprising at least 10 wt. % EPA and at least 10 wt. % DHA; or
    (b) borage oil comprising at least 20 wt. % GLA; or
    (c) a combination of (a) and (b) in a 1: 1 ratio;
  (2) 0.4 to 15 wt.% SDG;
  (3) 0.75 to 10 wt.% soy lecithin: and
  (4) at least 0.2 wt.% antioxidant combination comprising rosemary extract, tocopherols, and citric acid."

Signed and Sealed this
Twenty-second Day of March, 2016

Michelle K. Lee
*Director of the United States Patent and Trademark Office*